(12) United States Patent
Yellin et al.

(10) Patent No.: US 11,576,779 B2
(45) Date of Patent: Feb. 14, 2023

(54) MITRAL OR TRICUSPID REPAIR SYSTEMS WITH MULTI-DIRECTIONAL ANCHORS

(71) Applicant: VALCARE, INC., Newport Beach, CA (US)

(72) Inventors: Nadav Yellin, Ramat Gan (IL); Guy Rogel, Haifa (IL); Yoav Rozen, Benyamina (IL); Raphael Benary, Tel Aviv (IL); Shuki Porath, Haifa (IL); Samuel M. Shaolian, Newport Beach, CA (US)

(73) Assignee: VALCARE, INC., Herzelyia Pituach (IL)

( * ) Notice: Subject to any disclaimer, the term of this patent is extended or adjusted under 35 U.S.C. 154(b) by 171 days.

(21) Appl. No.: 15/923,677

(22) Filed: Mar. 16, 2018

(65) Prior Publication Data

US 2019/0091022 A1 Mar. 28, 2019

Related U.S. Application Data

(60) Provisional application No. 62/472,633, filed on Mar. 17, 2017.

(51) Int. Cl.
*A61F 2/24* (2006.01)
*A61B 17/064* (2006.01)
(Continued)

(52) U.S. Cl.
CPC .......... *A61F 2/2448* (2013.01); *A61B 17/064* (2013.01); *A61F 2/2445* (2013.01); *A61F 2/2466* (2013.01); *A61B 17/0401* (2013.01); *A61B 2017/00783* (2013.01); *A61B 2017/0641* (2013.01); *A61F 2/2427* (2013.01); (Continued)

(58) Field of Classification Search
CPC .................. A61F 2/2445; A61F 2/2448; A61F 2220/0016; A61F 2220/0025; A61B 2017/00783
See application file for complete search history.

(56) References Cited

U.S. PATENT DOCUMENTS 4,602,911 A 7/1986 Ahmadi et al.
5,236,440 A 8/1993 Hlavacek
(Continued)

FOREIGN PATENT DOCUMENTS

DE 102014102653 A1 9/2015
EP 2600799 A2 6/2013
(Continued)

OTHER PUBLICATIONS

Communication pursuant to Article 94(3) EPC for EP 14801009.3 dated Sep. 27, 2018.
(Continued)

*Primary Examiner* — Paul B Prebilic
(74) *Attorney, Agent, or Firm* — Dorsey & Whitney LLP

(57) ABSTRACT

Prosthetic ring valve assemblies are disclosed. A prosthetic valve ring assembly includes an outer tube and a plurality of anchors. The outer tube includes a plurality of windows. The plurality of anchors are positioned inside the outer tube and about a perimeter of the outer tube. The plurality of anchors are configured to be emitted from the plurality of windows in order to anchor the prosthetic valve ring assembly to annulus tissue of a patient.

6 Claims, 13 Drawing Sheets

(51) Int. Cl.
*A61B 17/04* (2006.01)
*A61B 17/00* (2006.01)

(52) U.S. Cl.
CPC ............... *A61F 2220/0016* (2013.01); *A61F 2220/0025* (2013.01)

(56) References Cited

U.S. PATENT DOCUMENTS

| | | |
|---|---|---|
| 5,306,296 A | 4/1994 | Wright et al. |
| 5,695,518 A | 12/1997 | Laerum |
| 5,716,370 A | 2/1998 | Williamson, IV et al. |
| 5,855,614 A | 1/1999 | Stevens et al. |
| 6,113,611 A | 9/2000 | Allen et al. |
| 6,231,602 B1 | 5/2001 | Carpentier et al. |
| 6,619,291 B2 | 9/2003 | Hlavka et al. |
| 6,629,534 B1 | 10/2003 | St. Goar et al. |
| 6,669,687 B1 | 12/2003 | Saadat |
| 6,689,048 B2 | 2/2004 | Vanden Hoek et al. |
| 6,726,704 B1 | 4/2004 | Loshakove et al. |
| 6,776,784 B2 | 8/2004 | Ginn |
| 6,790,229 B1 | 9/2004 | Berreklouw |
| 6,797,002 B2 | 9/2004 | Spence et al. |
| 6,805,711 B2 | 10/2004 | Quijano et al. |
| 6,893,459 B1 | 5/2005 | Macoviak |
| 7,101,395 B2 | 9/2006 | Tremulis et al. |
| 7,114,953 B1 | 10/2006 | Wagner |
| 7,175,660 B2 | 2/2007 | Cartledge et al. |
| 7,238,191 B2 | 7/2007 | Bachmann |
| 7,285,087 B2 | 10/2007 | Moaddeb et al. |
| 7,297,150 B2 | 11/2007 | Cartledge et al. |
| 7,569,072 B2 | 8/2009 | Berg et al. |
| 7,594,887 B2 | 9/2009 | Moaddeb et al. |
| 7,635,329 B2 | 12/2009 | Goldfarb et al. |
| 7,655,040 B2 | 2/2010 | Douk et al. |
| 7,717,954 B2 | 5/2010 | Solem et al. |
| 7,722,668 B2 | 5/2010 | Moaddeb et al. |
| 7,758,637 B2 | 7/2010 | Starksen et al. |
| 7,837,729 B2 | 11/2010 | Gordon et al. |
| 7,988,725 B2 | 8/2011 | Gross et al. |
| 8,163,014 B2 | 4/2012 | Lane et al. |
| 8,182,529 B2 | 5/2012 | Gordon et al. |
| 8,236,049 B2 | 8/2012 | Rowe et al. |
| 8,287,591 B2 | 10/2012 | Keidar et al. |
| 8,518,107 B2 | 8/2013 | Tsukashima et al. |
| 8,579,968 B1 | 11/2013 | Shannon et al. |
| 9,180,008 B2 * | 11/2015 | Yellin ............... A61F 2/2448 |
| 2002/0151961 A1 | 10/2002 | Lashinski |
| 2002/0151970 A1 | 10/2002 | Garrison et al. |
| 2002/0188170 A1 | 12/2002 | Santamore et al. |
| 2002/0198526 A1 | 12/2002 | Shaolian et al. |
| 2003/0050693 A1 | 3/2003 | Quijano et al. |
| 2003/0078465 A1 | 4/2003 | Pai et al. |
| 2003/0078671 A1 | 4/2003 | Lesniak et al. |
| 2003/0191528 A1 | 10/2003 | Quijano et al. |
| 2003/0198605 A1 | 10/2003 | Montgomery |
| 2003/0199974 A1 | 10/2003 | Lee et al. |
| 2004/0044364 A1 | 3/2004 | DeVries et al. |
| 2004/0068276 A1 | 4/2004 | Golden et al. |
| 2004/0122514 A1 | 6/2004 | Fogarty et al. |
| 2004/0138744 A1 | 7/2004 | Lashinski et al. |
| 2004/0148021 A1 | 7/2004 | Cartledge et al. |
| 2004/0193191 A1 | 9/2004 | Starksen et al. |
| 2004/0243230 A1 | 12/2004 | Navia et al. |
| 2004/0249391 A1 | 12/2004 | Cummins |
| 2004/0260393 A1 | 12/2004 | Rahdert et al. |
| 2004/0260394 A1 | 12/2004 | Douk et al. |
| 2005/0020696 A1 | 1/2005 | Montgomery et al. |
| 2005/0033325 A1 | 2/2005 | May et al. |
| 2005/0065550 A1 | 3/2005 | Starksen et al. |
| 2005/0090846 A1 | 4/2005 | Pedersen et al. |
| 2005/0096740 A1 | 5/2005 | Langberg et al. |
| 2005/0113910 A1 | 5/2005 | Paniagua et al. |
| 2005/0137692 A1 | 6/2005 | Haug et al. |
| 2005/0137695 A1 | 6/2005 | Salahieh et al. |
| 2005/0203549 A1 | 9/2005 | Realyvasquez |
| 2005/0222678 A1 | 10/2005 | Lashinski et al. |
| 2005/0240200 A1 | 10/2005 | Bergheim |
| 2005/0267572 A1 | 12/2005 | Schoon et al. |
| 2005/0283190 A1 | 12/2005 | Huitema et al. |
| 2005/0288778 A1 | 12/2005 | Shaoulian et al. |
| 2005/0288781 A1 | 12/2005 | Moaddeb et al. |
| 2006/0009737 A1 | 1/2006 | Whiting et al. |
| 2006/0020327 A1 | 1/2006 | Lashinski |
| 2006/0122633 A1 * | 6/2006 | To ................... A61B 17/00234 606/139 |
| 2006/0129025 A1 | 6/2006 | Levine et al. |
| 2006/0155165 A1 | 7/2006 | Vanden Hoek et al. |
| 2006/0161169 A1 | 7/2006 | Nieminen et al. |
| 2006/0184240 A1 | 8/2006 | Jimenez et al. |
| 2006/0184242 A1 | 8/2006 | Lichtenstein |
| 2006/0195134 A1 | 8/2006 | Crittenden |
| 2006/0195183 A1 | 8/2006 | Navia et al. |
| 2006/0241748 A1 | 10/2006 | Lee et al. |
| 2006/0282161 A1 | 12/2006 | Huynh et al. |
| 2007/0016287 A1 | 1/2007 | Cartledge et al. |
| 2007/0027533 A1 | 2/2007 | Douk |
| 2007/0038296 A1 | 2/2007 | Navia et al. |
| 2007/0051377 A1 | 3/2007 | Douk et al. |
| 2007/0067027 A1 | 3/2007 | Moaddeb et al. |
| 2007/0073098 A1 | 3/2007 | Lenker et al. |
| 2007/0080188 A1 | 4/2007 | Spence et al. |
| 2007/0093854 A1 | 4/2007 | Kayan |
| 2007/0118215 A1 | 5/2007 | Moaddeb |
| 2007/0128132 A1 | 6/2007 | Piergallini et al. |
| 2007/0135913 A1 | 6/2007 | Moaddeb et al. |
| 2007/0142907 A1 | 6/2007 | Moaddeb et al. |
| 2007/0213812 A1 | 9/2007 | Webler et al. |
| 2007/0233239 A1 | 10/2007 | Navia et al. |
| 2007/0239272 A1 | 10/2007 | Navia et al. |
| 2007/0244553 A1 | 10/2007 | Rafiee et al. |
| 2007/0244554 A1 | 10/2007 | Rafiee et al. |
| 2007/0244555 A1 | 10/2007 | Rafiee et al. |
| 2007/0244556 A1 | 10/2007 | Rafiee et al. |
| 2007/0250161 A1 | 10/2007 | Dolan |
| 2007/0293942 A1 | 12/2007 | Mirzaee |
| 2008/0177380 A1 | 7/2008 | Starksen et al. |
| 2008/0177381 A1 | 7/2008 | Navia et al. |
| 2008/0200980 A1 | 8/2008 | Robin et al. |
| 2008/0243220 A1 | 10/2008 | Barker |
| 2008/0262513 A1 | 10/2008 | Stabler et al. |
| 2008/0262609 A1 | 10/2008 | Gross et al. |
| 2008/0306586 A1 | 12/2008 | Cartledge et al. |
| 2009/0088838 A1 | 4/2009 | Shaolian et al. |
| 2009/0118747 A1 | 5/2009 | Bettuchi et al. |
| 2009/0125098 A1 | 5/2009 | Chuter |
| 2009/0149872 A1 | 6/2009 | Gross et al. |
| 2009/0216322 A1 | 8/2009 | Le et al. |
| 2009/0222083 A1 | 9/2009 | Nguyen et al. |
| 2009/0238778 A1 | 9/2009 | Mordas et al. |
| 2009/0299470 A1 | 12/2009 | Rao et al. |
| 2010/0010616 A1 | 1/2010 | Drews et al. |
| 2010/0030014 A1 | 2/2010 | Ferrazzi |
| 2010/0063586 A1 | 3/2010 | Hasenkam et al. |
| 2010/0121433 A1 | 5/2010 | Bolling et al. |
| 2010/0161047 A1 | 6/2010 | Cabiri |
| 2010/0185274 A1 | 7/2010 | Moaddeb et al. |
| 2010/0211166 A1 | 8/2010 | Miller et al. |
| 2010/0249920 A1 | 9/2010 | Bolling et al. |
| 2010/0266989 A1 | 10/2010 | Piergallini et al. |
| 2010/0280605 A1 | 11/2010 | Hammer et al. |
| 2010/0286767 A1 | 11/2010 | Zipory et al. |
| 2011/0022168 A1 | 1/2011 | Cartledge |
| 2011/0027753 A1 | 2/2011 | Maurat et al. |
| 2011/0034953 A1 | 2/2011 | Milo |
| 2011/0066231 A1 | 3/2011 | Cartledge et al. |
| 2011/0093062 A1 | 4/2011 | Cartledge et al. |
| 2011/0106245 A1 | 5/2011 | Miller et al. |
| 2011/0106247 A1 | 5/2011 | Miller et al. |
| 2011/0137397 A1 | 6/2011 | Chau et al. |
| 2011/0166649 A1 | 7/2011 | Gross et al. |
| 2011/0190879 A1 | 8/2011 | Bobo et al. |
| 2011/0208298 A1 | 8/2011 | Tuval et al. |
| 2011/0224785 A1 | 9/2011 | Hacohen |
| 2011/0257728 A1 | 10/2011 | Kuehn |

(56) References Cited

U.S. PATENT DOCUMENTS

| | | |
|---|---|---|
| 2011/0282361 A1 | 11/2011 | Miller et al. |
| 2011/0301698 A1 | 12/2011 | Miller et al. |
| 2011/0301699 A1 | 12/2011 | Saadat |
| 2012/0022557 A1 | 1/2012 | Cabiri et al. |
| 2012/0022644 A1 | 1/2012 | Reich et al. |
| 2012/0059458 A1 | 4/2012 | Buchbinder et al. |
| 2012/0095455 A1 | 4/2012 | Rodmond et al. |
| 2012/0123531 A1 | 5/2012 | Fsukashima et al. |
| 2012/0136436 A1 | 5/2012 | Cabiri et al. |
| 2012/0165930 A1 | 6/2012 | Gifford et al. |
| 2012/0245604 A1 | 9/2012 | Tegzes |
| 2012/0310330 A1 | 12/2012 | Buchbinder et al. |
| 2013/0087598 A1 | 4/2013 | Surti |
| 2013/0116780 A1 | 5/2013 | Miller et al. |
| 2013/0166022 A1 | 6/2013 | Conklin |
| 2013/0204361 A1 | 8/2013 | Adams et al. |
| 2013/0226289 A1 | 8/2013 | Shaolian et al. |
| 2013/0226290 A1 | 8/2013 | Yellin et al. |
| 2013/0282114 A1 | 10/2013 | Schweich, Jr. et al. |
| 2013/0289718 A1 | 10/2013 | Tsukashima et al. |
| 2013/0289720 A1 | 10/2013 | Dobrilovic |
| 2013/0304197 A1 | 11/2013 | Buchbinder et al. |
| 2014/0005778 A1 | 1/2014 | Buchbinder et al. |
| 2014/0046433 A1 | 2/2014 | Kovalsky |
| 2014/0058505 A1 | 2/2014 | Bielefeld |
| 2014/0114407 A1 | 4/2014 | Rajamannan |
| 2015/0173897 A1 | 6/2015 | Raanani et al. |
| 2015/0351903 A1 | 12/2015 | Morriss et al. |
| 2016/0022419 A1 | 1/2016 | Yellin et al. |
| 2016/0038286 A1 | 2/2016 | Yellin et al. |
| 2016/0089235 A1 | 3/2016 | Yellin |
| 2016/0106420 A1 | 4/2016 | Foerster et al. |
| 2016/0120642 A1 | 5/2016 | Shaolian et al. |
| 2016/0120645 A1 | 5/2016 | Alon |
| 2016/0331534 A1 | 11/2016 | Buchbinder et al. |
| 2017/0042670 A1 | 2/2017 | Shaolian et al. |
| 2017/0231763 A1 | 8/2017 | Yellin |
| 2018/0042723 A1 | 2/2018 | Yellin et al. |
| 2018/0161160 A1 | 6/2018 | Shaolian et al. |
| 2018/0161161 A1 | 6/2018 | Yellin et al. |

FOREIGN PATENT DOCUMENTS

| | | |
|---|---|---|
| EP | 2967700 A1 | 1/2016 |
| KR | 20040095482 A | 11/2004 |
| RU | 125062 U1 | 2/2013 |
| WO | 9009153 A1 | 2/1990 |
| WO | 9009153 A1 | 8/1990 |
| WO | 03017874 A1 | 3/2003 |
| WO | 03047467 A1 | 6/2003 |
| WO | 2005046488 A2 | 5/2005 |
| WO | 2009052427 A1 | 4/2009 |
| WO | 2009120764 A2 | 10/2009 |
| WO | 2010004546 A1 | 1/2010 |
| WO | 2010085659 A1 | 7/2010 |
| WO | 2011011443 A2 | 1/2011 |
| WO | 2011097355 A2 | 8/2011 |
| WO | 2012004679 A2 | 1/2012 |
| WO | 2012019052 A2 | 2/2012 |
| WO | 2012063228 A1 | 5/2012 |
| WO | 2012095159 A2 | 7/2012 |
| WO | 2012106354 A1 | 8/2012 |
| WO | 2012167095 A2 | 12/2012 |
| WO | 2013095816 A1 | 6/2013 |
| WO | 2013128436 A1 | 9/2013 |
| WO | 2013130641 A1 | 9/2013 |
| WO | 2013175468 A2 | 11/2013 |
| WO | 2014089424 A1 | 6/2014 |
| WO | 2014145399 A1 | 9/2014 |
| WO | 2014189509 A1 | 11/2014 |
| WO | 2014190329 A1 | 11/2014 |
| WO | 2014210600 A2 | 12/2014 |
| WO | 2015132668 A1 | 9/2015 |
| WO | 2018035118 A1 | 2/2018 |
| WO | 2018170424 A1 | 9/2018 |

OTHER PUBLICATIONS

European Search Report in EP 17155803.4 dated Aug. 9, 2017.
International Search Report and Written Opinion for PCT/US2014/044920 dated Dec. 24, 2014.
International Search Report and Written Opinion for PCT/US2011/046659 dated Jun. 4, 2012.
International Search Report and Written Opinion for PCT/US2012/040481 dated Dec. 6, 2012.
International Search Report and Written Opinion for PCT/US2013/042275 dated Feb. 20, 2014.
International Search Report and Written Opinion for PCT/US2013/073552 dated Mar. 6, 2014.
International Search Report and Written Opinion for PCT/US2014/039545 dated Oct. 22, 2014.
International Search Report and Written Opinion for PCT/US2014/030163 dated Aug. 27, 2014.
International Search Report and Written Opinion for PCT/US2013/058102 dated Apr. 21, 2014.
International Search Report for PCT/US2013/028065 dated Jun. 27, 2013.
Lendlein et al. Biodegradable, Elastic Shape-Memory Polymers for Potential Biomedical Applications (May 31, 2002), Science 296:1673-1676.
Supplemental European Search Report and Written Opinion for EP 12793292.9 dated Dec. 1, 2014.
Supplemental European Search Report and Written Opinion for EP 14762806.9 dated Jul. 29, 2016.
Supplementary Partial European Search Report for EP 13755441 dated Nov. 3, 2015.
International Search Report and Written Opinion for PCT/US17/46933 dated Dec. 21, 2017.
International Search Report and Written Opinion for PCT2019/064289 dated Feb. 5, 2020.
International Search Report and Written Opinion for PCT/US2018/022910 dated May 23, 2018.
13860442.6, Extended European Search Report, dated Aug. 11, 2016, 7 pages.
19151726.7, Extended European Search Report, dated Jul. 22, 2019, 9 pages.
PCT/US2014/039454, International Search Report and Written Opinion, dated Oct. 22, 2014, 10 pages.
PCT/US2019/064289, International Search Report and Written Opinion, dated Feb. 5, 2020.

\* cited by examiner

MITRAL OR TRICUSPID REPAIR SYSTEMS
WITH MULTI-DIRECTIONAL ANCHORS

CROSS-REFERENCE TO RELATED
APPLICATIONS

The present application claims benefit of priority under 35 U.S.C. 119(e) to the filing date of U.S. Provisional Patent Application 62/472,633 filed Mar. 17, 2017, entitled, "IMPROVED MITRAL OR TRICUSPID VALVE REPAIR SYSTEM," the contents of which is incorporated herein by reference in their entirety.

TECHNICAL FIELD

The present disclosure relates to implantable prosthetic devices. More specifically, the disclosure is directed to an improved prosthetic device implantable by catheter for the treatment of mitral or tricuspid regurgitation.

BACKGROUND

Mitral Regurgitation is a valvular dysfunction that causes blood volume to flow during systole (during left ventricular contraction) from the left ventricle to the left atrium. In contrast, in a healthy heart, this direction of flow is blocked by the mitral valve. The reverse flow during systole causes pressure to rise in the left atrium, and maintaining a normal cardiac output results in an increased pressure in the left ventricle.

Treating patients with MR (mitral regurgitation) or TR (tricuspid regurgitation) could require valve replacement in order to reduce or eliminate the regurgitation. For many years, the commonly accepted treatment was surgical repair or replacement of the native valve during open heart surgery. In recent years, a trans-vascular technique has been developed for introducing and implanting a prosthetic heart valve using a flexible catheter in a manner that is less invasive than open heart surgery.

In the trans-vascular technique, a prosthetic valve is delivered to the target site (e.g., aortic valve, mitral valve, tricuspid valve, or other valve) through a catheter while the valve is crimped to a low diameter shaft. The valve is then expanded/deployed to a functional size when it is located in the correct position. Examples of such prosthetic valves, and related processes for delivering the valves through a catheter, are described in U.S. Pat. No. 8,518,107, the content of which is hereby incorporated by reference in its entirety.

Advancing the catheter to the target site can be achieved through: (a) The vascular system where a catheter is advanced from the femoral vein/artery, or any other blood vessel that allows access to the target site; (b) Trans-apically where a catheter is advanced through a small incision made in the chest wall and then through the apex; or (c) Trans-atrially where a catheter is advanced through a small incision made in the chest wall and then through the left or right atrium.

SUMMARY

Embodiments herein are directed to various prosthetic valve ring assemblies for use in repairing cardiac valves suffering from, for example, mitral or tricuspid regurgitation.

A prosthetic valve ring assembly is described herein. In certain embodiments, the prosthetic valve ring assembly can include an outer tube that includes a plurality of windows; and a plurality of anchors positioned inside the outer tube and about a perimeter of the outer tube. The plurality of anchors are configured to be emitted from the plurality of windows to anchor the prosthetic valve ring assembly to annulus tissue of a patient. In some embodiments, the anchors are configured to be emitted in different directions. For example, a first portion of the anchors are configured to be emitted to a ventricular side of the annulus tissue of the patient and a second portion of the anchors are configured to be emitted to an atrial side of the annulus tissue of the patient.

In some embodiments, the anchors are created using a laser cutting technique. In an embodiment, the laser cutting technique includes cutting according to a laser cut pattern to define a plurality of windows through which the plurality of anchors are configured to be emitted.

In some embodiments, the prosthetic valve ring assembly further includes a closure device configured to lock a distal side and a proximal side of the prosthetic valve ring assembly. In some embodiments, the prosthetic valve ring assembly further includes a post adjustment mechanism that includes a flexible connection configured to move an anterior portion of the prosthetic valve ring assembly relative to a posterior portion of the prosthetic valve ring assembly, thereby changing at least one of a size and a geometry of the prosthetic valve ring assembly.

In some embodiments, the prosthetic valve ring assembly further includes a closure device configured to lock a distal side and a proximal side of the prosthetic valve ring assembly; and an unlocking mechanism configured to unlock the closure device, thereby enabling repositioning or retrieval of the prosthetic valve ring assembly from a patient through a catheter. In some embodiments, the prosthetic valve ring assembly further includes one or more bumps positioned on a perimeter of the prosthetic valve ring assembly and configured to apply additional pressure to trigones of the annulus tissue of the patient, thereby providing improved anchoring of the prosthetic valve ring assembly.

BRIEF DESCRIPTION OF THE DRAWINGS

Aspects, features, benefits and advantages of the embodiments described herein will be apparent with regard to the following description, appended claims, and accompanying drawings where:

DETAILED DESCRIPTION

Figure 1:
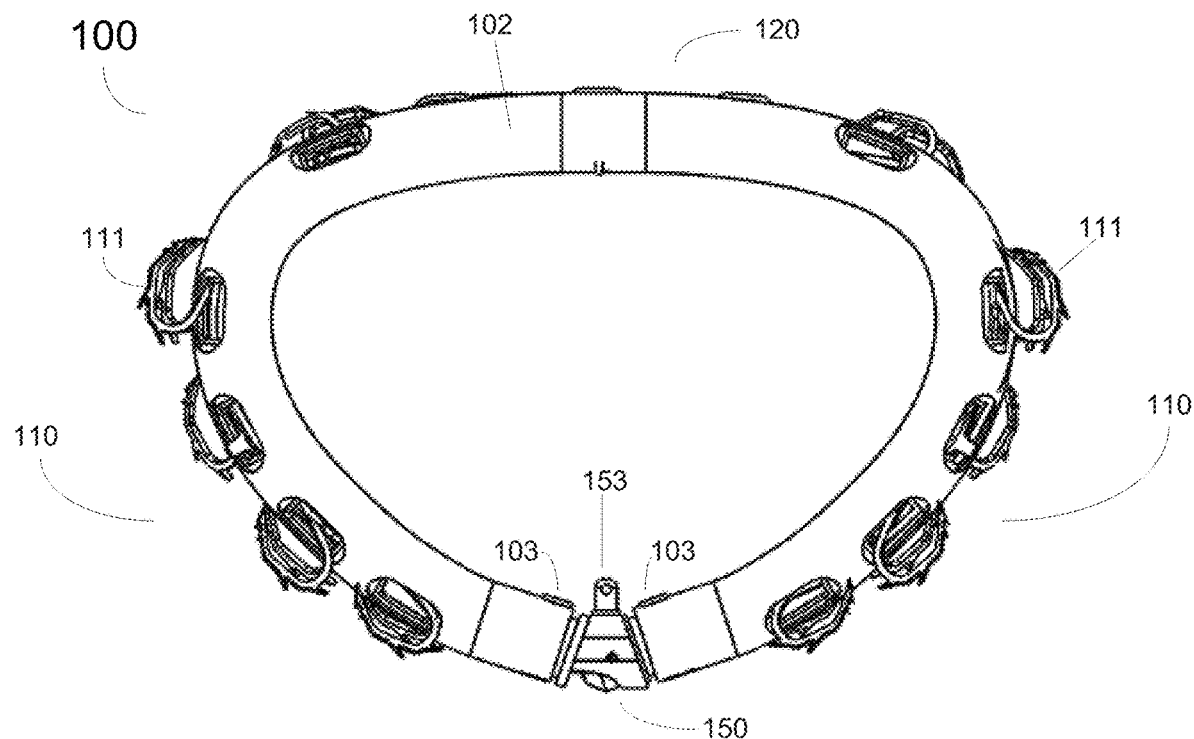
FIG. 1 illustrates a top view of an improved mitral valve ring, in accordance with at least one embodiment of the present disclosure.

This disclosure is not limited to the particular systems, devices and methods described, as these may vary. The terminology used in the description is for the purpose of describing the particular versions or embodiments only, and is not intended to limit the scope.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

When implanting a replacement valve (e.g., an aortic valve, mitral valve, tricuspid valve, or other valve), the replacement valve can include a prosthesis attachment. The prosthesis can be configured to secure the replacement valve in a patient's heart. An example of such a prosthesis is the AMEND™ Mitral Valve Repair Annuloplasty ring developed by Valcare Medical. The AMEND™ ring is a D-shaped ring configured to emulate the total valve replacement for patients who suffer from Mitral Regurgitation (MR, as described above). Additional detail related to prosthetic valves for mitral or tricuspid valve replacement can be found in U.S. patent application Ser. No. 14/891,189 entitled "Transcatheter Prosthetic Valve for Mitral or Tricuspid Valve Replacement," filed May 22, 2013, the content of which is incorporated herein by reference in its entirety.

As described herein, a prosthetic ring can be configured to include various anchor zones on a posterior side. The anchor zones are positioned to emit anchors in different directions and/or angles from two or more windows on the cross section of the ring. For example, a portion of the anchors may be emitted to the ventricular side of the annulus tissue, and a portion of the anchors may be emitted to the atrial side of the annulus tissue. Such an arrangement can provide for improved anchoring of the ring into the annulus tissue as compared to conventional mitral valve rings.

It should be noted that, while the following detailed description of the figures is directed to a prosthetic ring configured to anchor a replacement valve such as the AMEND™ ring as described above, the techniques, ideas, and processes described herein can be applied to any mitral valve ring.

FIGS. 1-4 illustrate various views of an improved mitral valve ring 100. In certain implementations, the ring 100 can include posterior side anchor zones that are configured to emit anchors in different directions and/or angles from two or more windows on the cross section of the ring. In some examples, a portion of the anchors are configured to be emitted to the ventricular side of a patient's annulus tissue, while a second portion of the anchors are configured to be emitted to the atrial side of the annulus tissue. Thus, two or more anchors can be emitted from one window in different directions.

FIG. 1 illustrates a top view of the ring assembly 100. The ring assembly 100 can include an outer tube 102 that defines the shape of the ring assembly. The outer tube 102 can include one or more windows about its circumference as well as one or more windows in its cross-section. One or more anchors can be positioned and configured to extend through these windows. The ring assembly 100 can also include a set of posterior zone anchors 110. As shown in FIG. 1, the posterior zone anchors 110 are generally positioned on the posterior of the ring assembly 100. The ring assembly 100 can further include anterior zone anchors 120 generally positioned on the anterior of the ring assembly.

Figure 2:
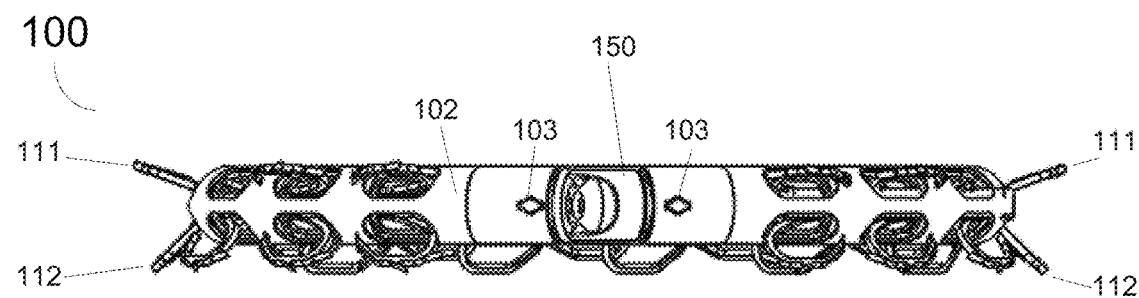
FIG. 2 illustrates a side view of an improved mitral valve ring, in accordance with at least one embodiment of the present disclosure.

Each anchor zone (including both posterior zone anchors 110 and anterior zone anchors 120) can include atrial side anchors 111 as well as ventricular side anchors 112 (not shown in FIG. 1 but illustrated in, for example, FIG. 2). As noted above, in certain implementations, upon insertion of the ring assembly 100, the atrial side anchors 111 can be configured to be emitted into the atrial side of the patient's annulus tissue and the ventricular side anchors can be configured to be emitted into the ventricular side of the patient's annulus tissue.

As further shown in FIG. 1, the ring assembly 100 can include a closure device 150. The closure device 150 can be configured to lock a distal end of the ring assembly 100 to a proximal end of the ring assembly. The closure device 150 can also be designed and configured to removably attach to a delivery system for the valve replacement implant. For example, in certain implementations, the closure device 150 can include a pivot pin 153 that is configured to removably attach the ring assembly 100 to a delivery device as well as provide for rotation of the ring assembly when emitted from the delivery device. For example, the pivot pin 153 can be configured to provide for 90 degrees of rotation of the ring assembly 100. In other implementations, the pivot pin can be configured to provide for additional ranges of rotation such as 75-105 degrees of rotation, 60-120 degrees of rotation, and other similar ranges of rotation.

The ring assembly 100 can further include a set of pins 103. The pins 103 can be positioned and configured to connect the outer tube 102 to the closure device 150. In certain implementations, the pins 103 can be further positioned and configured to provide for routing of sutures as well as to function as a pulley while providing for rotation of a suture (e.g., 90 degree rotation) with minimal friction.

FIG. 2 illustrates a first side view of the ring assembly 100, shown from the posterior and further illustrating the closure device 150. FIG. 2 further illustrates the alternative emitting direction of the atrial side anchors 111 in an outward and upward direction relative to a plane of the ring assembly 100 and the ventricular side anchors 112 in an outward and downward direction relative to the plane of the ring assembly 100.

Figure 3:
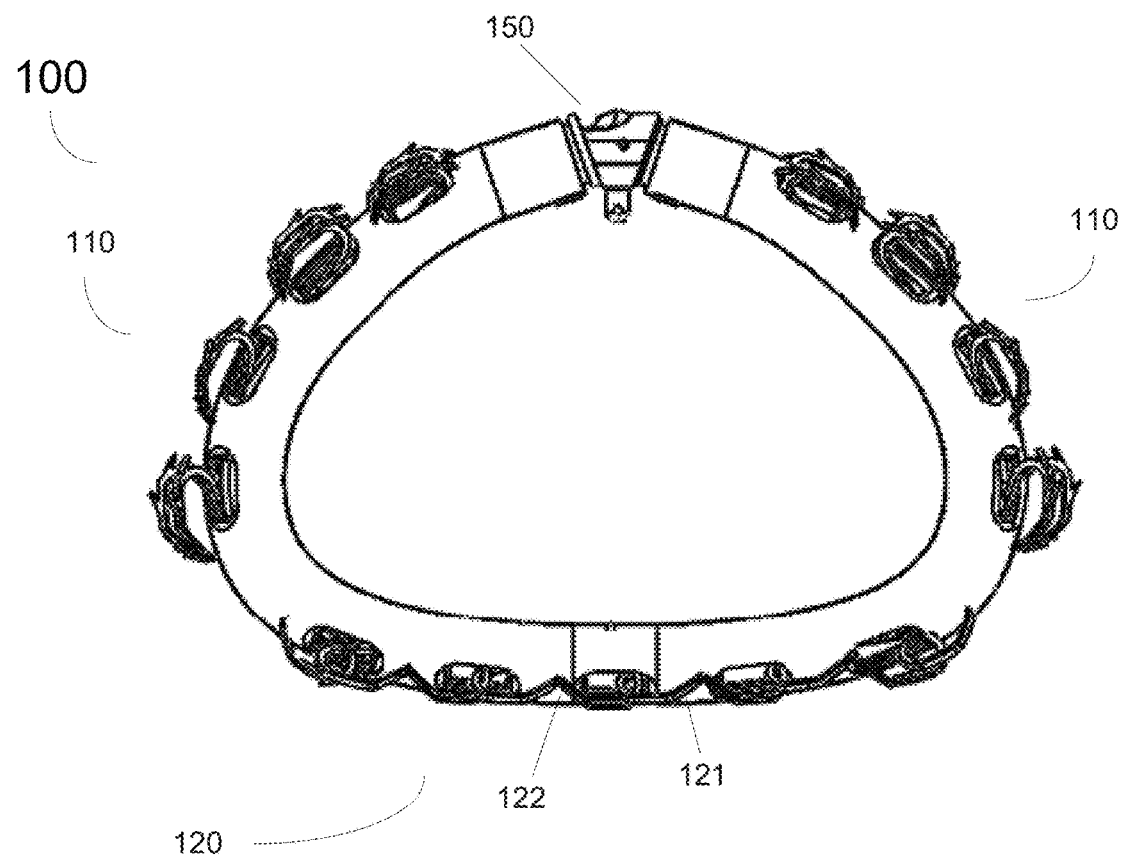
FIG. 3 illustrates a bottom view of an improved mitral valve ring, in accordance with at least one embodiment of the present disclosure.

FIG. 3 illustrates a bottom view of the ring assembly 100. In contrast to FIG. 1, FIG. 3 illustrates the ventricular side anchors 112. FIG. 3 further illustrates additional anterior side anchors 120 that were obscured from view in FIG. 1.

Additionally, in certain embodiments, various anchors can be configured such that portions of the anchors can cross one another in different directions, thereby creating a closed loop and stapling effect of the tissue. For example, anchors 121 and 122 as shown in FIG. 3 are configured to cross one another in different directions, thereby having a stapling effect on the adjacent tissue, securely locking the ring assembly 100 into position.

Figure 4:
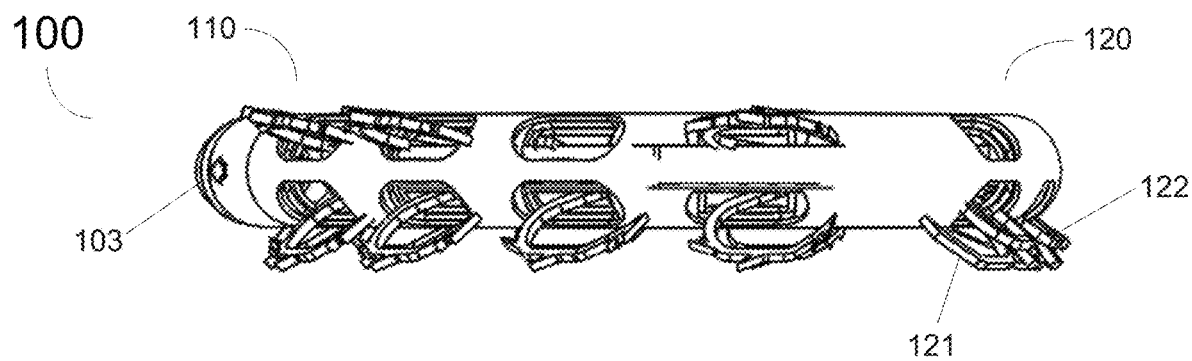
FIG. 4 illustrates another side view of an improved mitral valve ring, in accordance with at least one embodiment of the present disclosure.

FIG. 4 illustrates a second side view of the ring assembly 100, shown further illustrating the crossing anchors 121 and 122.

The raw materials of the ring assembly 100 and various components included therein can be selected from various materials, such as various polymers, shape memory materials such as Nitinol, metals such as stainless steel, or other similar materials safe for implanting; into or adjacent to living tissue. In certain implementations, the ring assembly 100 can include a combination of two or more different materials, such as stainless steel 316/316L and Nitinol. This combination is provided by way of example only, and other materials can be used alternately or additionally.

Figure 5:
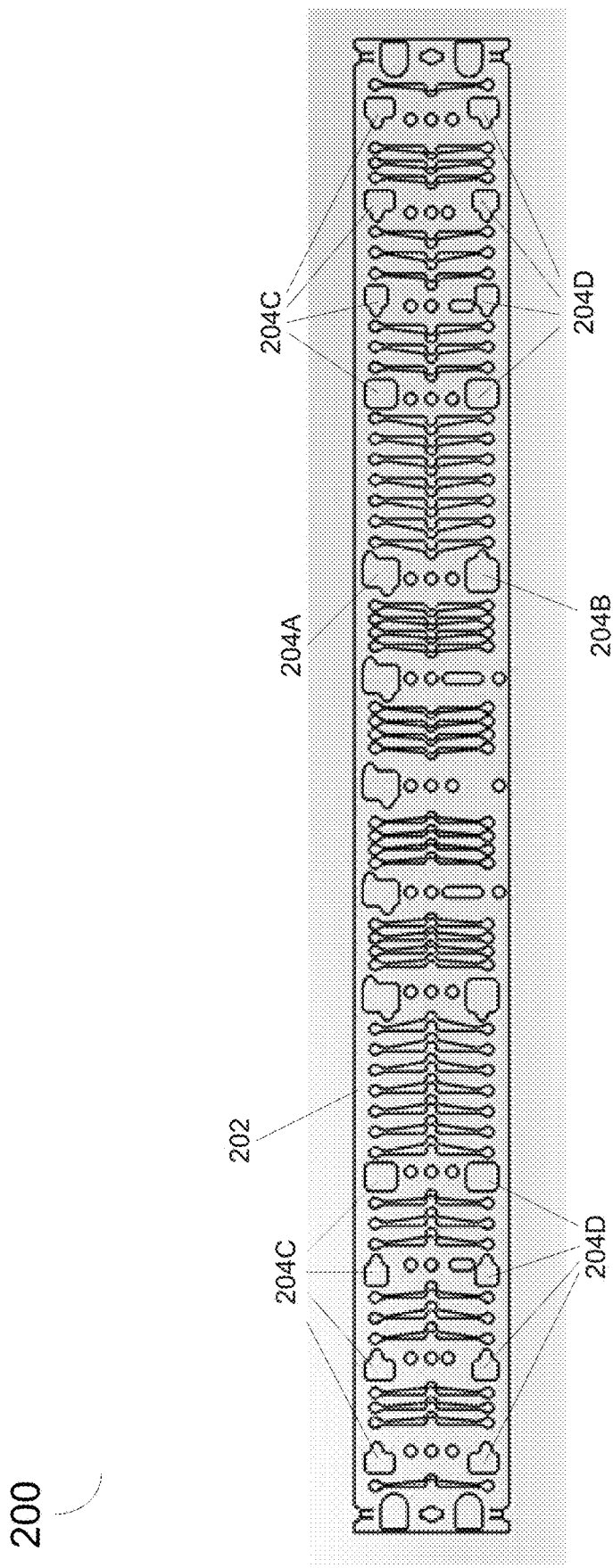
FIG. 5 illustrates a ring laser cut pattern, in accordance with at least one embodiment of the present disclosure.

In order to create the ring assembly 100 as described above, the outer tube 102 can be manufactured such that multiple windows are defined. The windows can be positioned to facilitate deployment of the various anchors as described above. FIG. 5 illustrates an example cut pattern 200 for creating the outer tube 102 as described above. For example, the pattern 200 shows an example cut pattern of a ring tube 202 with several windows 204A, 204B, 204C and 204D that allow deployment of anchors in different directions. For example, anchors can be emitted in the atrial side from windows 204D, and anchors can be emitted from the ventricular side from windows 204C.

In an alternate embodiment, more than one anchor can be emitted from one window with one or more anchors in the atrial side and one or more anchors in ventricular side. In another embodiment, one or more anchors can be emitted from different windows in the same direction. For example, two windows (e.g., 204A and 204B) can be configured to provide for simultaneous deployment of anchors towards the ventricular side.

Figure 6:
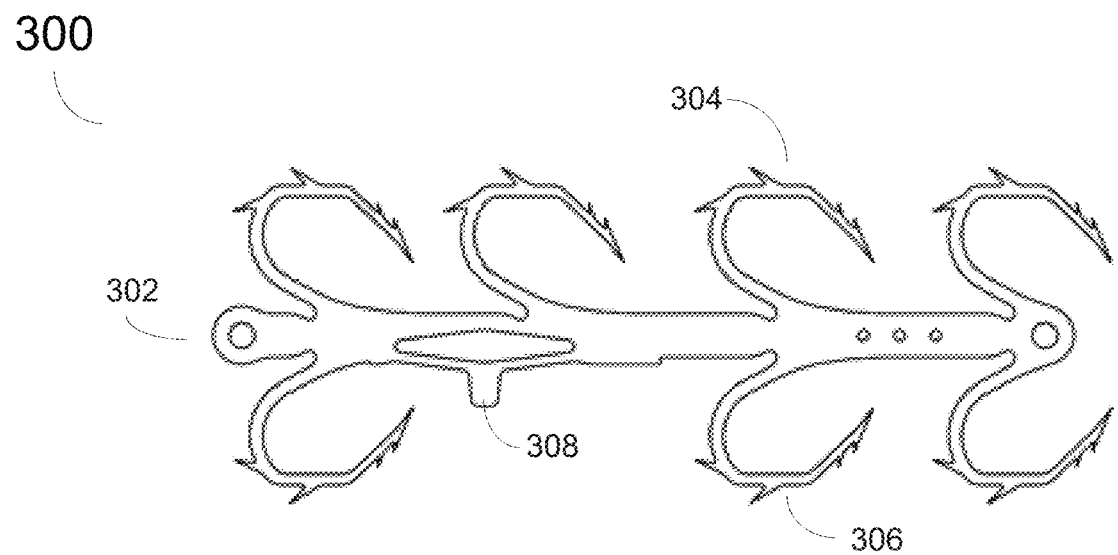
FIG. 6 illustrates a posterior anchor zone with anchors activated by passive anchor stop features, in accordance with at least one embodiment of the present disclosure.
Figure 7:
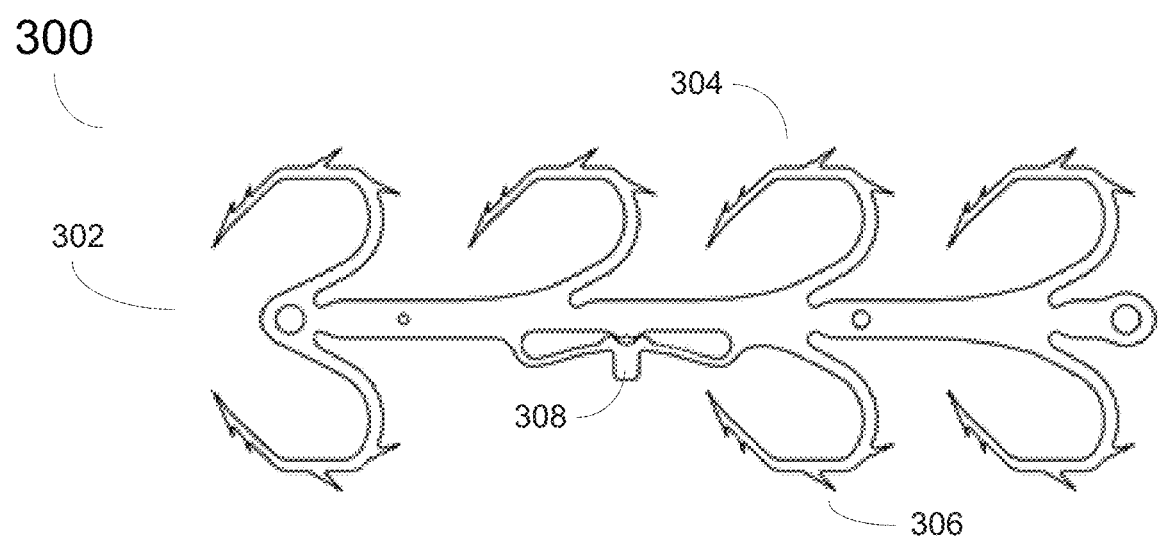
FIG. 7 illustrates a posterior anchor zone with anchors activated by active anchor stop features, in accordance with at least one embodiment of the present disclosure.

FIGS. 6 and 7 illustrate example cut patterns (e.g., laser cut patterns) for the anterior and/or posterior zone anchors such as posterior zone anchors 110 and anterior zone anchors 120 as described above. Additionally, as noted above, anchors can be emitted in both the atrial and ventricle directions, such as atrial anchors 111 and ventricle anchors 112 as described above.

To achieve such a configuration, cut pattern 300 as shown in FIGS. 6 and 7 can be used to create one or more anchor zones 302. The cut pattern can define a set of atrial anchors 304 and a set of ventricle anchors 306 within the anchor zone 302. The cut pattern 300 can also define an anchor stop feature 308. The anchor stop feature 308 can be configured to lock the anchor zone 302 into, for example, the outer tube of a ring assembly to prevent unintentional movement of the anchor zone.

In certain implementations, the anchor stop feature 308 can be a passive feature that is activated as a result of a force exerted on the anchor zone 302 (e.g., a pulling force) causing a bending or other change to the geometry of the anchor stop feature 308. In other embodiments, the anchor stop feature 308 can include an associated activation mechanism that facilitates activation of the anchor stop feature. For example, the activation mechanism can be an activation pulley that prevents the anchor stop feature 308 from bending of otherwise deforming such that a portion of the anchor stop feature exits through a corresponding hole on the outer tube of the ring assembly. Such an arrangement can lock the anchor zone 302 into position as the anchor stop feature 308 prevents any relative movement. In some examples, pulling on the activator mechanism and removing it from the designated location allows the anchor stop feature 308 to bend and allows relative movement of the anchor zone 302 in relation to the outer tube of the ring assembly.

In certain implementations, the anchor stop feature 308 can be located in either the ventricular side or atrial side of the anchor zone 320 and/or outer tube. Additionally, in various embodiments, the anchor stop feature 308 can be positioned in any location along the anchor zone 302. The position as shown in FIGS. 6 and 7 is shown by way of example only.

It should be noted that laser cutting the ring assemblies as described herein is provided by way of example only, and additional manufacturing techniques can be used. For example, a stamping process can be used to stamp the cut patterns as described above.

Figure 8:
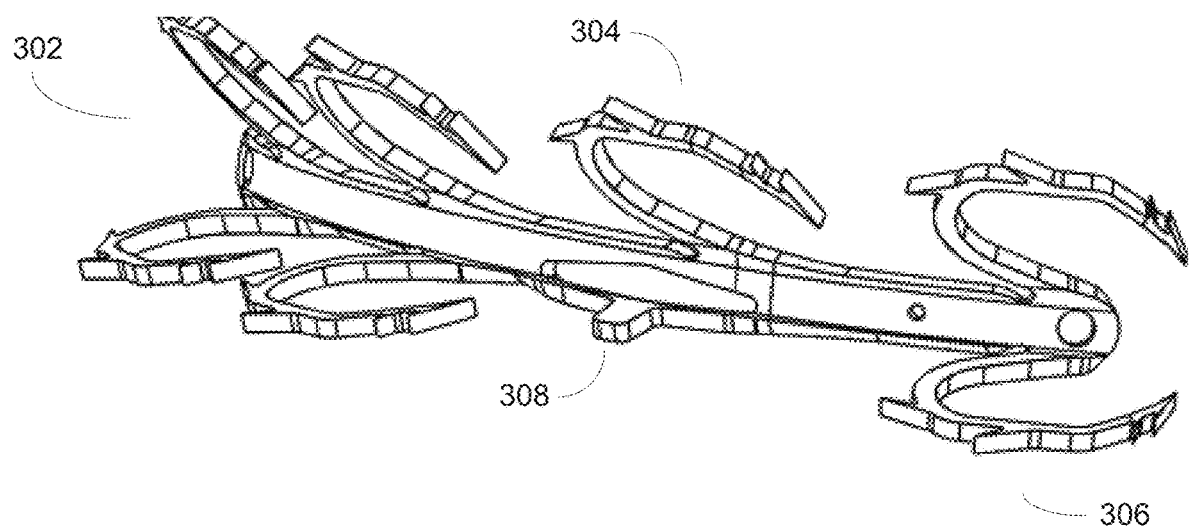
FIG. 8 illustrates the 3D shape of posterior and/or anterior zone anchors, in accordance with at least one embodiment of the present disclosure.
Figure 9:
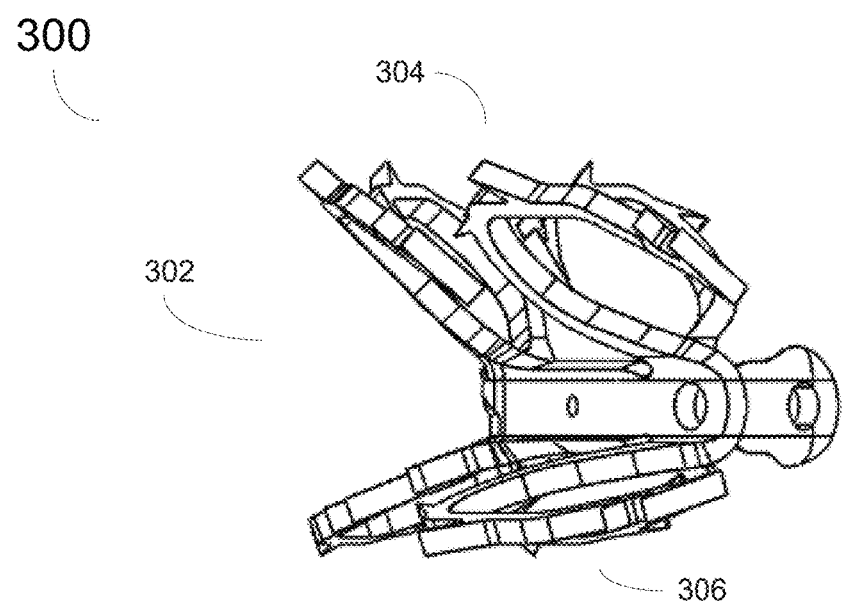
FIG. 9 illustrates the angles of posterior and/or anterior zone anchors, in accordance with at least one embodiment of the present disclosure

FIGS. 8 and 9 illustrate the cut patterns 300 as described above in regard to FIGS. 6 and 7 that have been, for example, heat treated and to include various bends and curves, thereby defining a specific three-dimensional shape for the anchor zones 302. For example, the anchor zones 302 can be heat-treated and bent at an angle selected from a range of angles. For example, in certain implementations the range of angles can be from zero degrees (e.g., no additional bending) to 135 degrees. As shown in FIGS. 8 and 9, the ventricle anchors 306 can be heat-treated to 45 degrees, and the atrial anchors 304 can be heat-treated to 60 degrees.

In addition, the anchor zone can have a 3D shape that fits the zone location in the final ring assembly. For example, the posterior anchor zones can be curved to fit the posterior curvature of the ring assembly, and the anterior anchor zones can be curved to fit the anterior curvature of the ring assembly.

It should be noted that heat-treated bending and curving is provided by way of example only. Depending upon the type of material being used and the design of the individual components such as the anchor zones, alternative bending and curving techniques can be used to form the anchor zones to the geometry of the final ring assembly.

Figure 10:
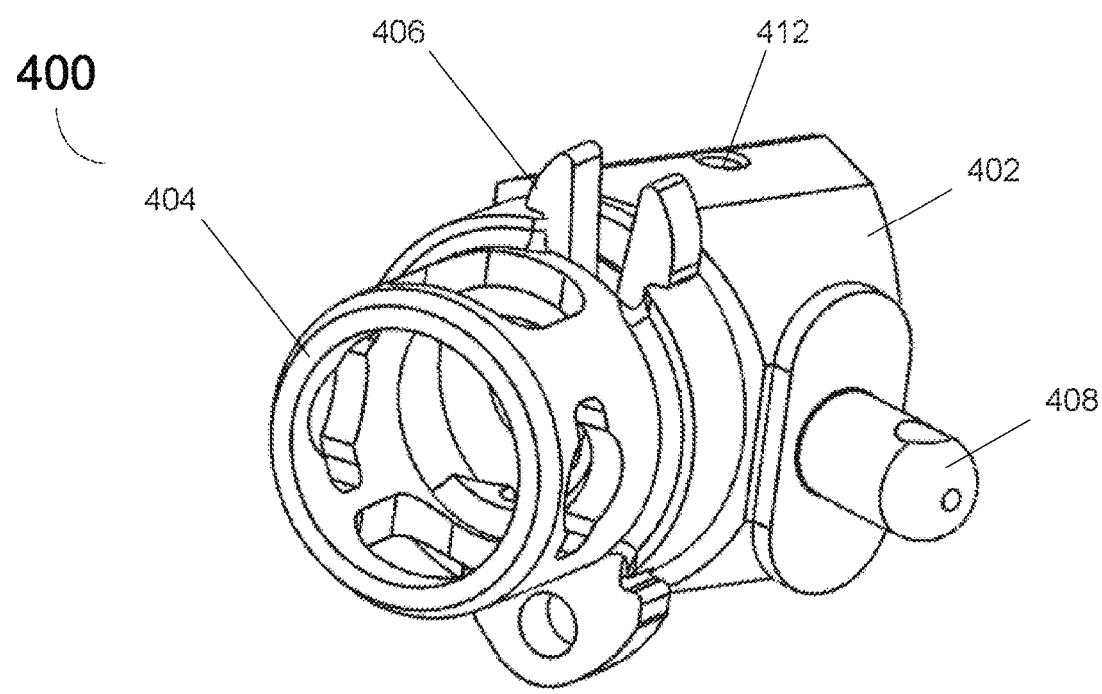
FIG. 10 illustrates a perspective view of a closure device, in accordance with at least one embodiment of the present disclosure.
Figure 11:
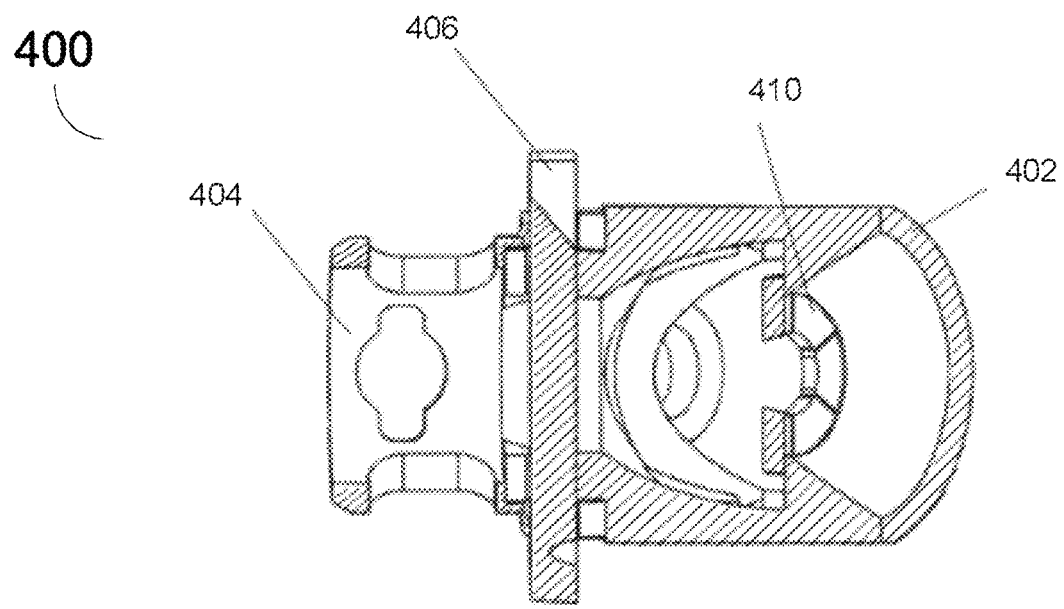
FIG. 11 illustrates a cross-sectional view of a closure device, in accordance with at least one embodiment of the present disclosure.
Figure 12:
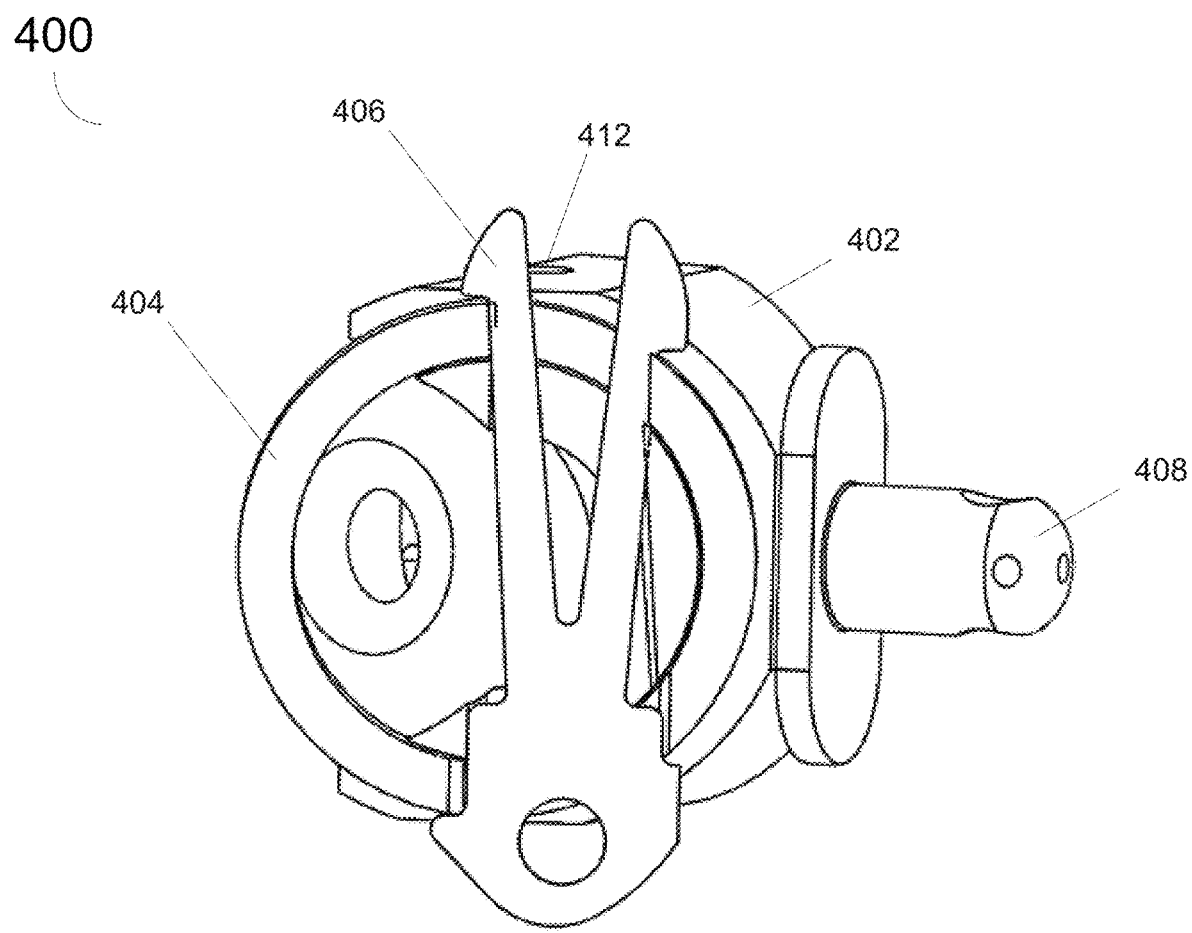
FIG. 12 illustrates another perspective view of a closure device, in accordance with at least one embodiment of the present disclosure.

FIGS. 10-12 illustrate detailed views of a closing mechanism 400 for a ring assembly, such as closing mechanism 150 as described above in regard to ring assembly 100. In certain implementations, a closing mechanism can include a female component configured to lock to a male component. For example, FIGS. 10-12 illustrate various views and embodiments of the female component 402. As shown in FIG. 10, the female component 402 can include a locking mechanism for releasably attaching to a male component or cup 404.

The female component 402 can further include an unsnapping pin 406. The unsnapping pin can be positioned and configured to unsnap or otherwise disconnect the female component 402 from the cup 404 of the ring assembly. Additionally, the female component 402 can include a pivot pin 408 for attaching the female component to an outer tube of the ring assembly. Additionally, the pivot pin 408 can be configured to function as an interface between the ring assembly and a delivery system, similar to pins 103 as described above.

FIG. 11 illustrates a cross-section of the female component 402. As shown in the cross-sectional view, the female component 402 can include a disk 410. The disk 410 can be positioned to abut an end of the cup 404 when inserted into the female component 402 to provide for locking of the male component to the female component. In some examples, the disk 410 can be held in position with a cover.

FIG. 12 illustrates a view of the locking mechanism 400 with a portion of the cup 404 removed, showing additional detail of the unsnapping pin 406. As shown in FIG. 12, the unsnapping pin 406 can be designed with two individual fingers extending from a central point such that, upon exerting a force (e.g., a squeezing force) upon an end of the fingers opposite the central point, the fingers deflect about the point. Upon deflection of the unsnapping pin 406, the unsnapping pin can be removed, thereby releasing the male component (e.g., cup 404) from the female component 402.

In certain implementations, the disk 410 and the unsnapping pin 406 can be made from a shape memory alloy such as Nitinol. In some example, the other components of the female component can be made from various metallic materials such as stainless steel, aluminum, Nitinol, and titanium.

As noted above, the cup 404 and the female component 402 are attached together with the unsnapping pin 406. If properly inserted and positioned, the unsnapping pin 406 can visually verify that the two parts are well-attached and cannot open unintentionally. Conversely, upon activation of the unsnapping pin 406 by pulling it in a specific direction, it allows separation of the two components. By doing this, the ring close structure is compromised and the closed shape becomes open and allows retrieval of the implant into the delivery system.

In some embodiments, the female component 402 can have one or more gold markers 412 that provide for confirmation of locking of the cup 404 and the female component during a clinical procedure.

Figure 13:
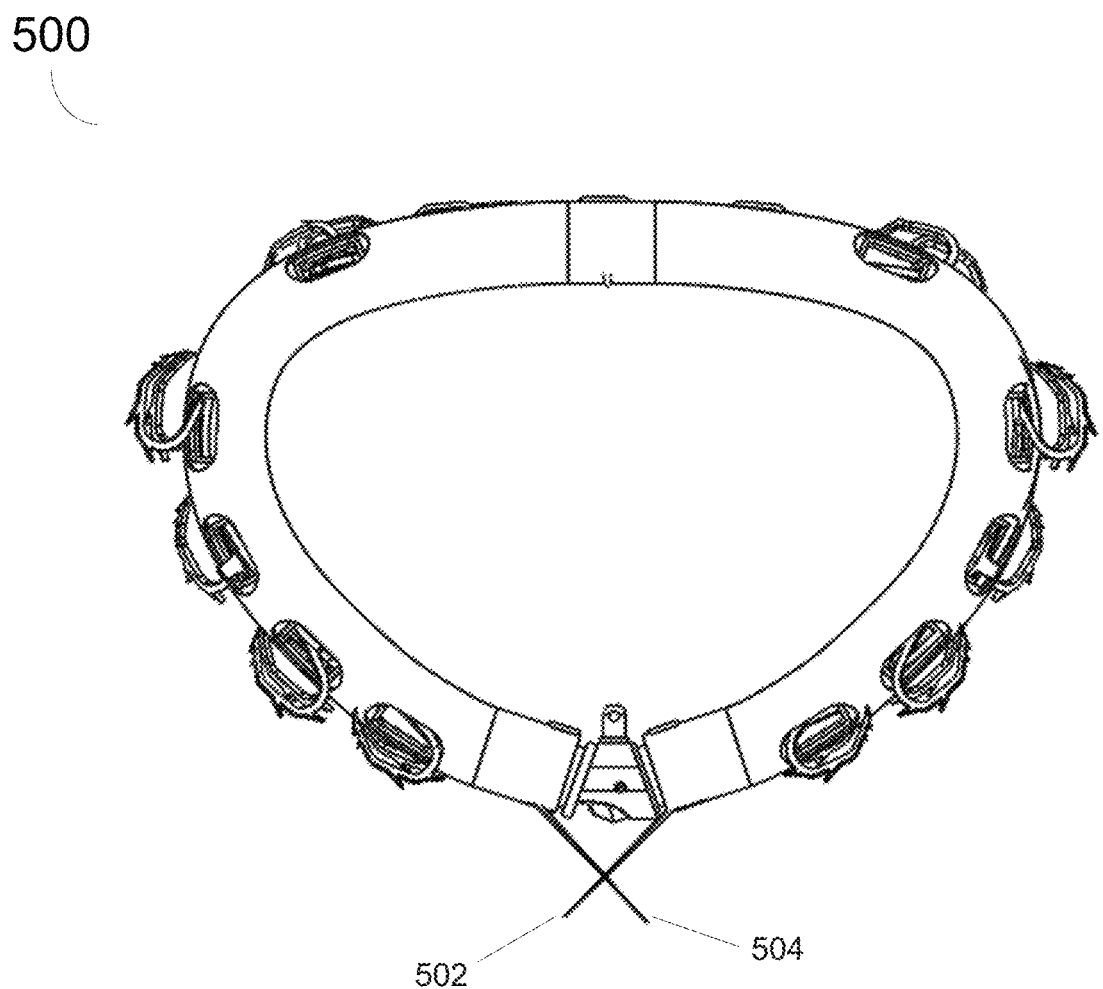
FIG. 13 illustrates a top view of a mitral valve ring that includes anchors adjacent to the closure device area, in accordance with at least one embodiment of the present disclosure.
Figure 14:
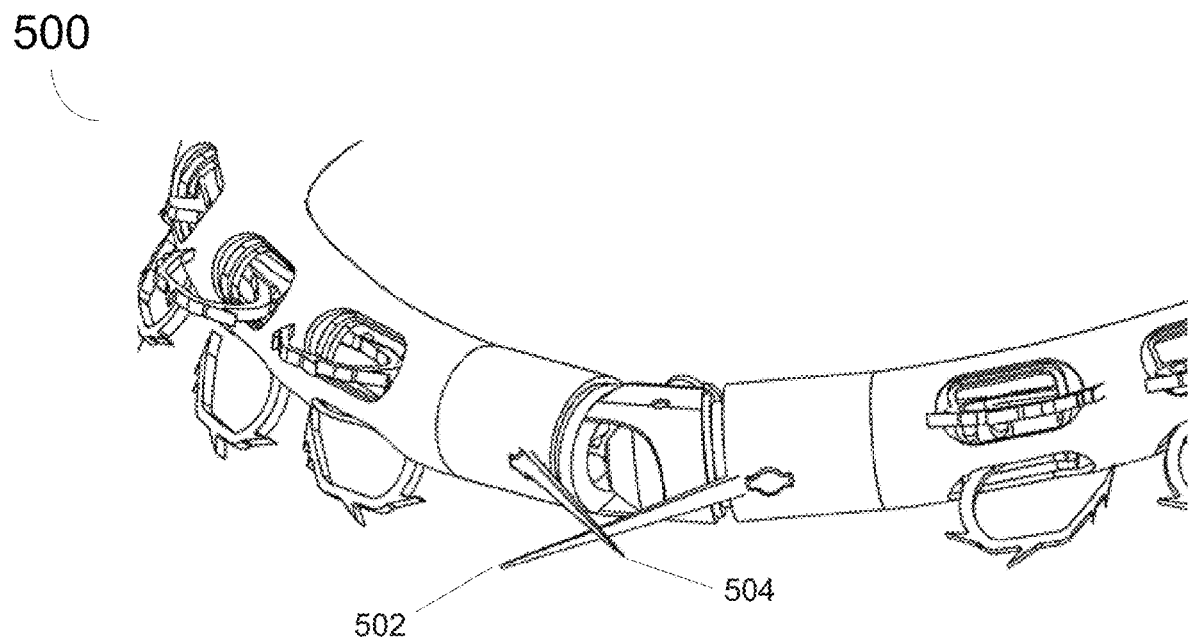
FIG. 14 illustrates an isometric view of a mitral valve ring that includes anchors adjacent to the closure device area, in accordance with at least one embodiment of the present disclosure.
Figure 15:
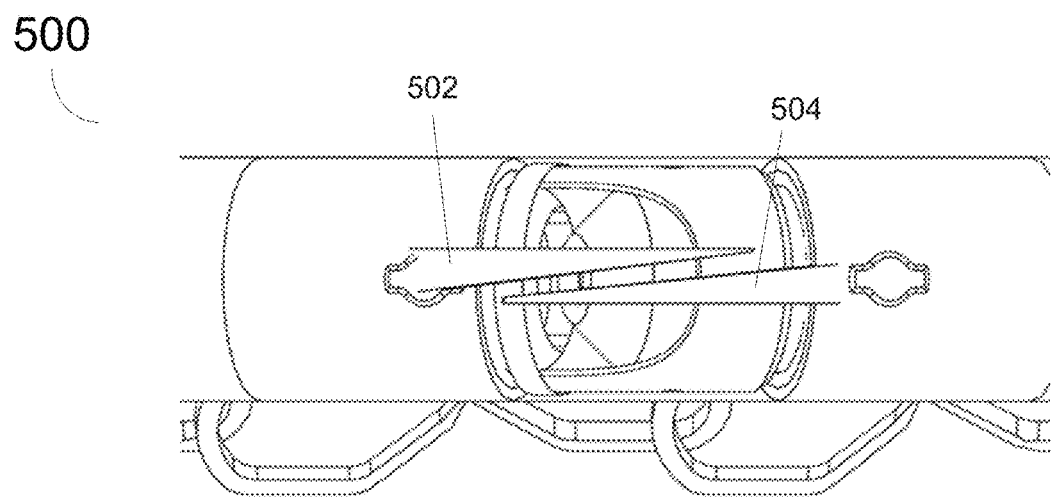
FIG. 15 illustrates a top side view of a mitral valve ring that includes anchors adjacent to the closure device area, in accordance with at least one embodiment of the present disclosure.

FIGS. 13-15 illustrate various views of a ring assembly 500. Similar to ring assembly 100 as described above, the ring assembly 500 can include an outer tube, a set of posterior zone anchors, a set of anterior zone anchors, and a closure device 150. However, the ring assembly 500 as shown in FIGS. 13-15 can further include additional anchors 502 and 504 positioned adjacent to the closure device and configured to improve attachment of the ring assembly 500 to the patient's posterior annulus tissue. In certain implementations, the anchors 502 and 504 can be configured to be emitted in different directions and/or angles from one or more windows on the cross section of the outer tube in the area of the closure device. In some examples, one or more additional anchors can be configured to be emitted to the ventricular side of the annulus tissue, and one or more of the additional anchors can be configured to be emitted to the atrial side of the annulus tissue. In some embodiments, two or more additional anchors can be configured to be emitted from one window in the outer tube in different directions to each other. In some embodiments, the anchors can include additional features such as hooks, barbs, or other similar features for increasing durability and preventing detachment.

Figure 16:
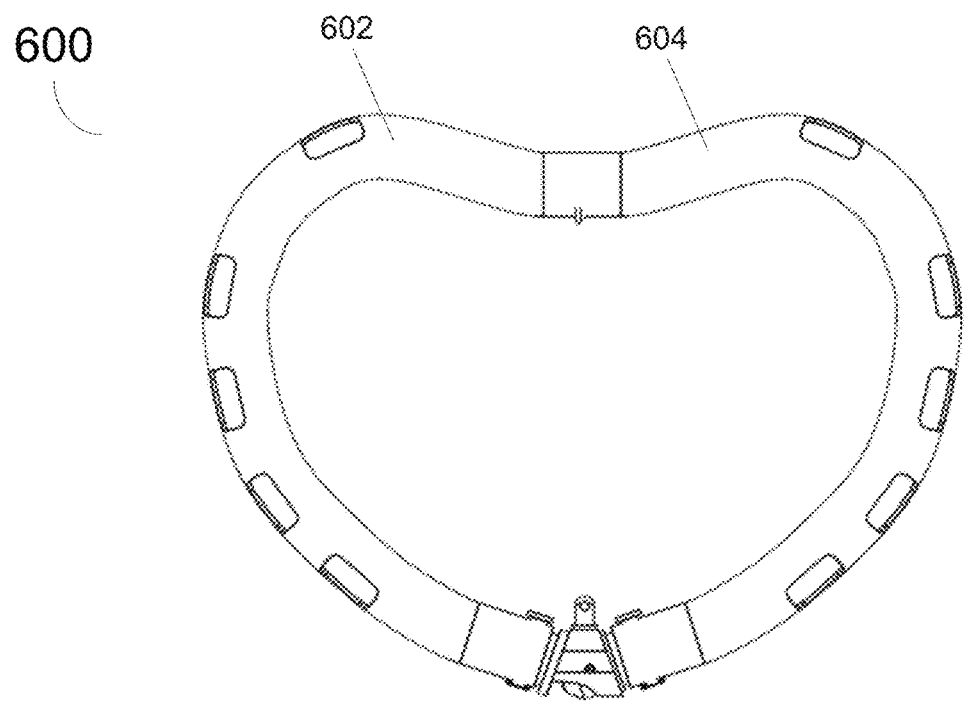
FIG. 16 illustrates a top view of an alternative ring assembly including bumps in the trigones region, in accordance with at least one embodiment of the present disclosure.
Figure 17:
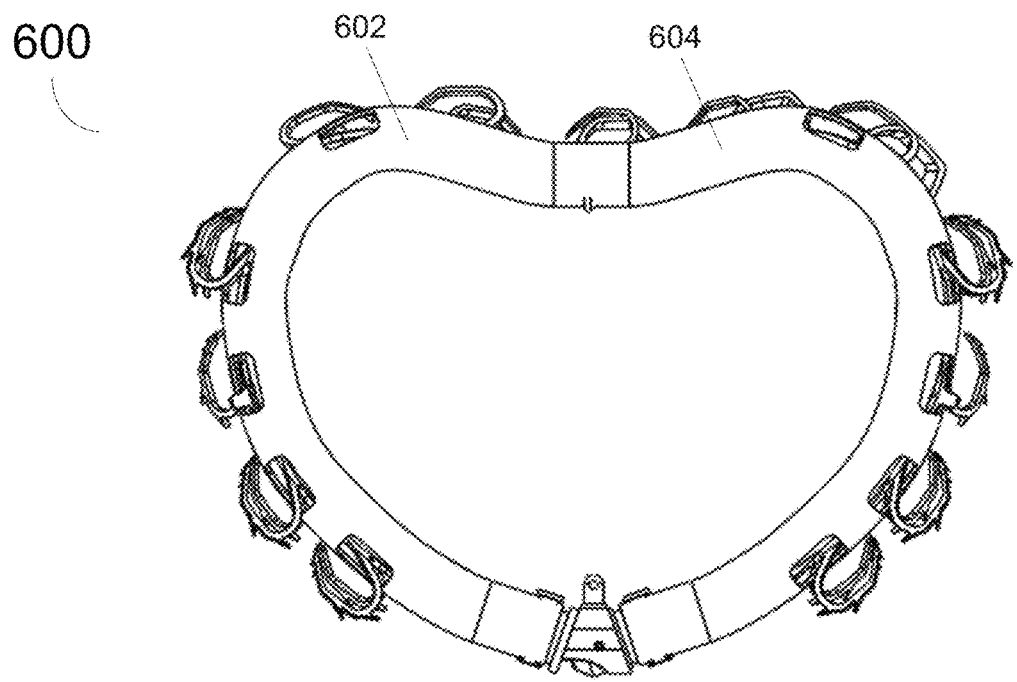
FIG. 17 illustrates a top view of an alternative ring assembly including bumps in the trigones region with anchors, in accordance with at least one embodiment of the present disclosure.

In certain implementations, a ring assembly can further include bumps or other similar protrusions in the trigones area of the ring assembly. For example, as shown in FIGS. 16 and 17, a ring assembly 600 (shown without anchors in FIG. 16 and with anchors in FIG. 17) can include bumps 602 and 604 positioned on the portion of the ring assembly that will be adjacent to the fibrous trigones region of a patient's heart. The bumps 602 and 604, or other similar protrusions or added features, can provide for added contact between the ring assembly 600 and the patient's trigones region of the annulus tissue. In some implementations, achieving such contact can provide for better contact between the ring assembly 600 and the annulus tissue as compared to a ring assembly without the bumps in the trigones region. Similar to the ring assemblies as described above, various patterns and directions of anchors can be used to improve anchoring the ring assembly 600 to the annulus tissue as well.

Figure 18:
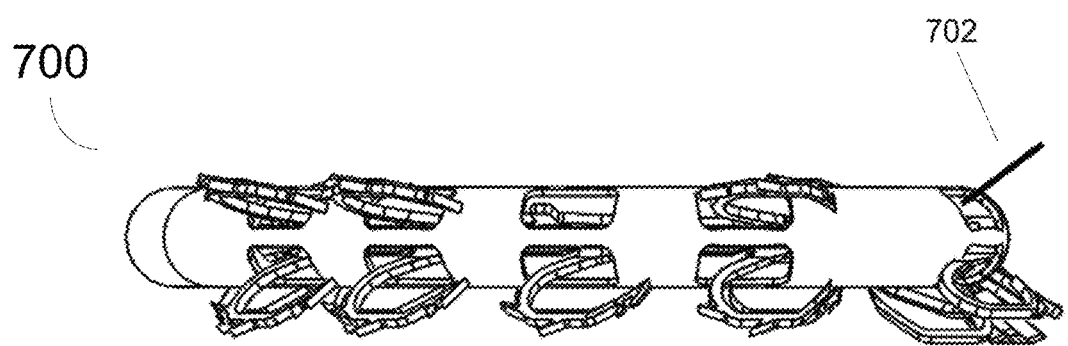
FIG. 18 illustrates a side view of an alternative ring assembly including bumps in the trigones region with anchors, in accordance with at least one embodiment of the present disclosure.
Figure 19:
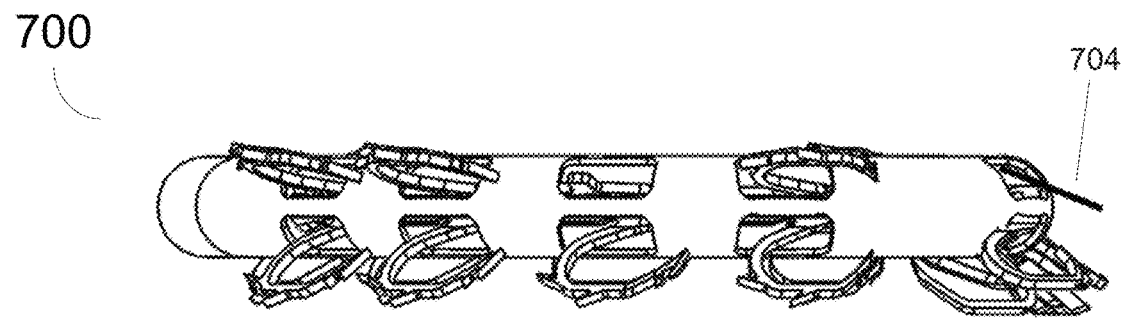
FIG. 19 illustrates another side view of an alternative ring assembly including bumps in the trigones region with anchors, in accordance with at least one embodiment of the present disclosure.
Figure 20:
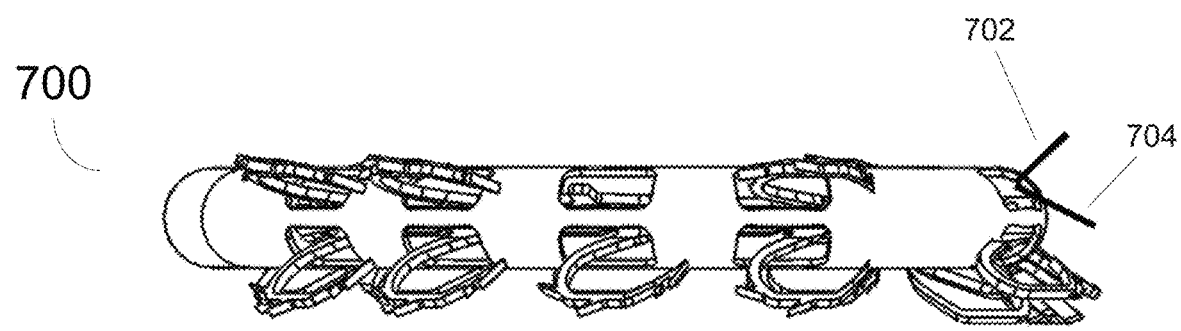
FIG. 20 illustrates yet another side view of an alternative ring assembly including bumps in the trigones region with anchors, in accordance with at least one embodiment of the present disclosure.

In certain implementations, additional anchors can be beneficial for providing additional anchoring points for a ring assembly. In some examples, a single anchor or set of additional anchors can be emitted from an existing window in an outer tube of a ring assembly providing a more robust anchoring point as compared to the curved anchors as described above. For example, as shown in FIGS. 18-20, ring assembly 700 can include additional anchors configured to provide a more robust anchoring point. As shown in FIG. 18, an additional anchor 702 can be emitted from a window for providing an additional anchoring point on the atrial side of the ring assembly 700. FIG. 19 illustrates an additional anchor 704 being emitted from a similar window for providing an additional anchoring point on the ventricular side of the ring assembly 700. FIG. 20 illustrates a set of two or more additional anchors emitting from a single window. In this example, additional anchors 702 and 704 provide additional anchoring into the atrial side and the ventricular side of the ring assembly 700 respectively.

In some implementations, resizing the ring assembly can be desirable as a single ring assembly can accommodate an additional range of patients and valve sizes. For example, a ring assembly can include a flexible connection that is laser cut from a similar material as the outer tube of the ring assembly. The flexible connection can be configured to contract and/or expand to allow for changing the size of the ring before, during, and/or after implantation of the ring assembly. In some examples, the ring assembly can be manufactured from separate segments or components that are configured to be attached together with a mechanism or device that controls expansion and/or contraction of each side of a ring assembly separately or simultaneously.

Figure 21:
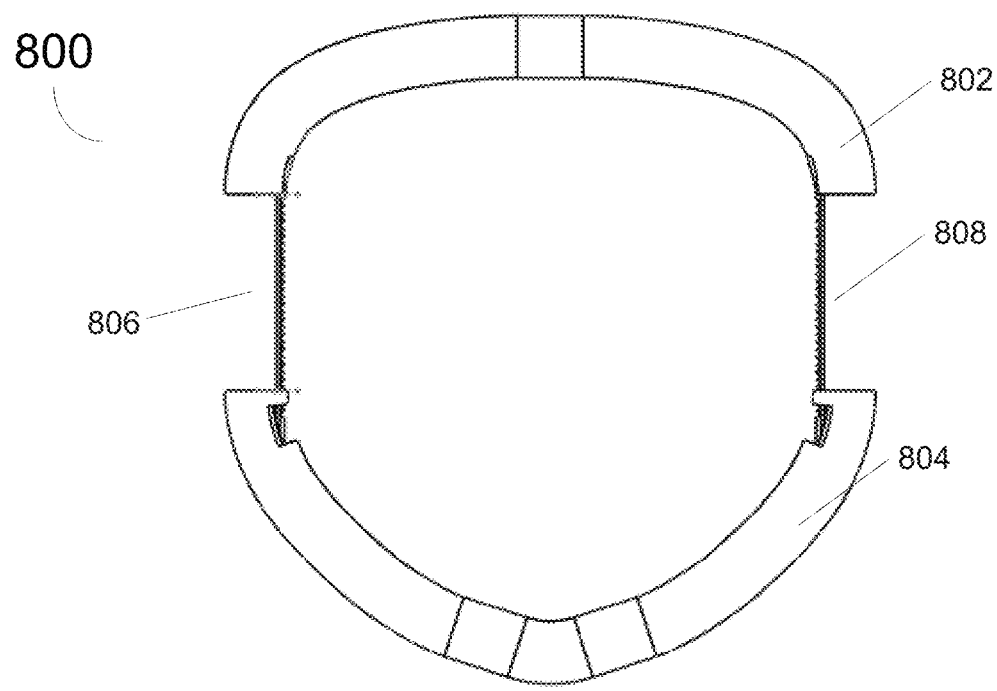
FIG. 21 illustrates an alternative mitral valve ring with one or more post adjustment mechanisms, in accordance with at least one embodiment of the present disclosure.

FIG. 21 illustrates a ring assembly 800 that is configured to be resizable as described above. The ring assembly 800 can include an anterior portion 802 and a posterior portion 804. The anterior portion 802 and the posterior portion 804 can be connected together with a set of adjustable components 806 and 808. The adjustable components 806 and 808 can be made from a flexible material configured to expand and/or contract, thereby changing the overall size of the ring assembly 800. In certain implementations, the anterior portion 802 and/or the posterior portion 804 can include an adjustment mechanism that is configured to interact with the adjustable components 806 and 808 to change the size, shape and/or geometry of the ring assembly 800. For example, the adjustment mechanisms can include a ratcheting feature that is configured to interact with the adjustable components 806 and 808 to change the size of the ring assembly 800.

It should be noted that a ratcheting feature is provided by way of example only. Additional adjustment mechanisms such as friction-based holding devices, snap-based devices, winding devices, and other similar adjustment devices can be used. Additionally, it should be noted that two adjustable components 806 and 808 are shown by way of example. In additional implementations, various numbers of adjustable components can be used. For example, a single adjustable component can be included on one side of the ring assembly.

Figure 22:
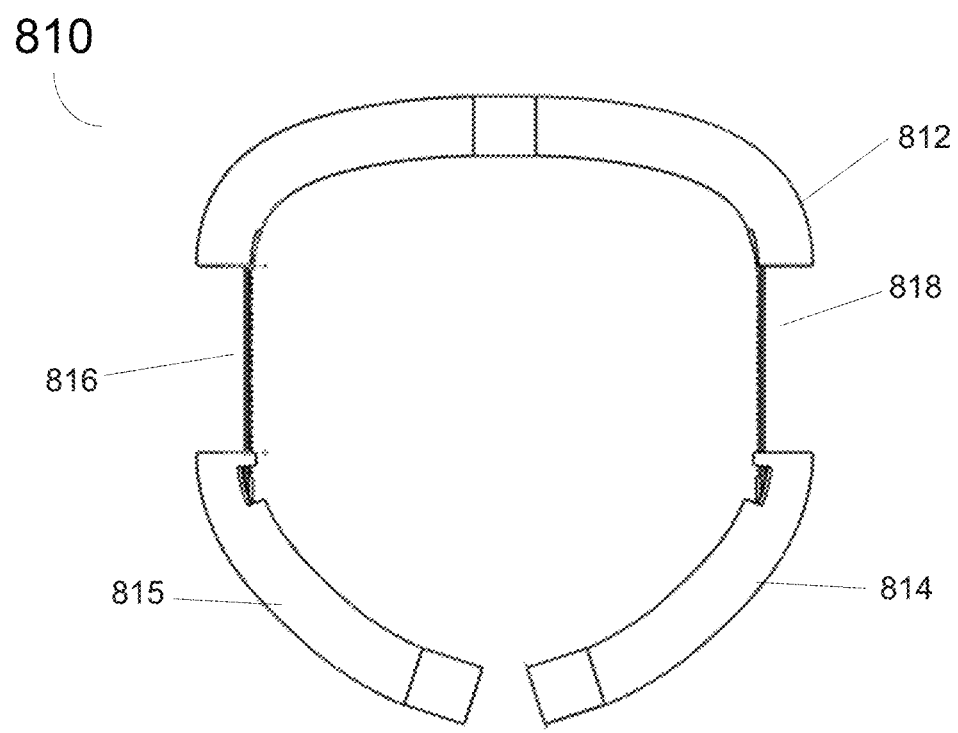
FIG. 22 illustrates another alternative mitral valve ring with one or more post adjustment mechanisms, in accordance with at least one embodiment of the present disclosure.

FIG. 22 illustrates a ring assembly 810 that is configured to be resizable, similar to ring assembly 800 as described above. However, the ring assembly 810 can include an anterior portion 812 and two posterior portions 814 and 815. Such an arrangement can provide for additional flexibility and sizing options when implanting the ring assembly 810.

In some implementations, the anterior portion 812 can be connected to the posterior portion 815 with a first adjustable component 816. Similarly, the anterior portion can be connected to the posterior portion 814 with a second adjustable component 818. The posterior portions 814 and 815 can be configured to releasably attach to one another via a closure device such as closure device 150 as described above.

The ring assemblies as described above can be designed and shaped for various functions such as mitral valve replacement. However, a similar ring assembly can be designed and constructed for tricuspid valve replacement as well. However, a tricuspid ring can be designed with additional features such as a release zone positioned on the ring assembly at a location that will be adjacent to a patient's atrioventricular node or valves.

Figure 23:
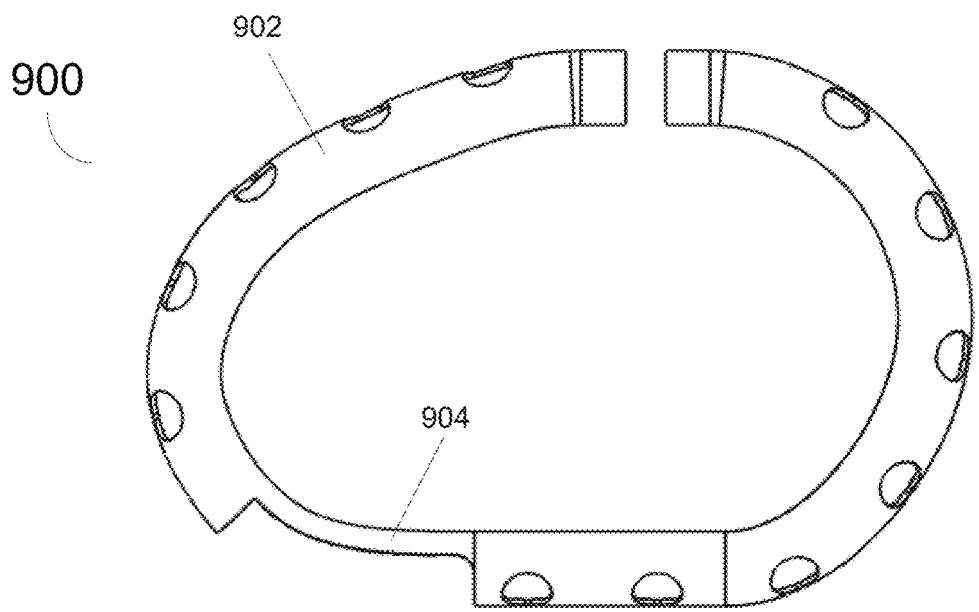
FIG. 23 illustrates a laser cut layout for a tricuspid ring, in accordance with at least one embodiment of the present disclosure.
Figure 24:
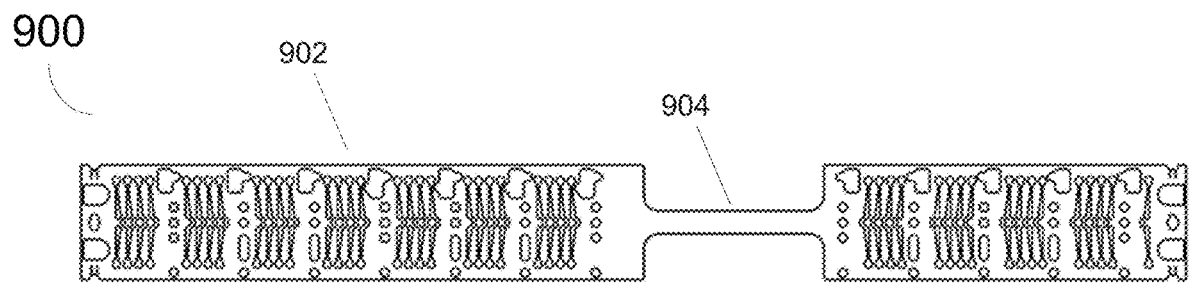
FIG. 24 illustrates a 3D shape for a tricuspid ring, in accordance with at least one embodiment of the present disclosure.

FIGS. 23 and 24 illustrate an example tricuspid ring assembly 900 (FIG. 23 illustrating a 3D view of the assembly, while FIG. 24 illustrates a flat cut pattern view). The outer tube 902 of the ring assembly 900 can include multiple windows through which anchors can be emitted as described above. However, the ring assembly 900 can further include a release zone 904 configured and positioned at a location that will be adjacent to a patient's atrioventricular node or valves when the ring assembly is implanted.

In certain implementations, the release zone 904 does not have any anchors. Rather, the alternate shape and profile of the release zone provides for interference between the ring assembly 900 and the patient's atrioventricular node or valves, thereby securing the ring assembly in position.

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," et cetera). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups. It will be further understood by those within the art that if a specific number of an introduced claim recitation is intended, such an intent will be explicitly recited in the claim, and in the absence of such recitation no such intent is present.

For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, et cetera" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, et cetera). In those instances where a convention analogous to "at least one of A, B, or C, et cetera" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, et cetera. As a non-limiting example, each range discussed herein can be readily broken down into a lower third, middle third and upper third, et cetera. As will also be understood by one skilled in the art all language such as "up to," "at least," and the like include the number recited and refer to ranges that can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A prosthetic valve ring assembly, comprising:
   an outer tube comprising a plurality of windows;
   a plurality of anchors positioned inside the outer tube and around a perimeter of the outer tube, wherein the plurality of anchors are configured to be emitted from the plurality of windows to anchor the prosthetic valve ring assembly to a patient's annulus tissue, and wherein a first portion of the plurality of anchors is configured to be emitted to an atrial side of the annulus tissue in an outward and upward direction relative to a plane of the outer tube, and a second portion of the plurality of anchors is configured to be emitted to a ventricular side of the annulus tissue in an outward and downward direction relative to the plane of the outer tube;
   a closure device configured to lock a distal end and a proximal end of the prosthetic valve ring assembly; and
   an unsnapping pin configured to unlock the closure device to separate the distal end and the proximal end of the prosthetic valve ring assembly, thereby providing for repositioning or retrieval of the prosthetic valve ring assembly from the patient through a catheter.

2. The prosthetic valve ring assembly of claim 1, wherein the plurality of anchors are created using a laser cutting technique.

3. The prosthetic valve ring assembly of claim 2, wherein the laser cutting technique comprises cutting according to a laser cut pattern to define a plurality of windows through which the plurality of anchors are configured to be emitted.

4. The prosthetic valve ring assembly of claim 1, further comprising a post adjustment mechanism comprising a flexible connection configured to move an anterior portion of the prosthetic valve ring assembly relative to a posterior portion of the prosthetic valve ring assembly, thereby changing at least one of a size and a geometry of the prosthetic valve ring assembly.

5. The prosthetic valve ring assembly of claim 1, further comprising one or more bumps positioned on a perimeter of the prosthetic valve ring assembly and configured to apply additional pressure to trigones of the patient's annulus tissue, thereby providing improved anchoring of the prosthetic valve ring assembly.

6. The prosthetic valve ring assembly of claim 1, wherein the closure device is interfaced to the outer tube by suture pins which are configured to function as pulleys for sutures.

* * * * *